United States Patent
Wang et al.

(10) Patent No.: US 10,139,801 B2
(45) Date of Patent: Nov. 27, 2018

(54) PARAFFIN DISPENSER, EMBEDDER, AND CONTROL METHOD AND CONTROL APPARATUS FOR PARAFFIN DISPENSER

(71) Applicant: Leica Microsystems Ltd., Shanghai, Shanghai (CN)

(72) Inventors: Chonglu Wang, Shanghai (CN); Ningjiang Chen, Shanghai (CN); Zhiwei Wu, Shanghai (CN)

(73) Assignee: Leica Microsystems Ltd., Shanghai, Shanghai (CN)

( * ) Notice: Subject to any disclaimer, the term of this patent is extended or adjusted under 35 U.S.C. 154(b) by 9 days.

(21) Appl. No.: 15/454,221

(22) Filed: Mar. 9, 2017

(65) Prior Publication Data

US 2017/0269568 A1 Sep. 21, 2017

(30) Foreign Application Priority Data

Mar. 15, 2016 (CN) .......................... 2016 1 0145856

(51) Int. Cl.
| | |
|---|---|
| G05B 19/12 | (2006.01) |
| B29C 39/00 | (2006.01) |
| B29C 39/24 | (2006.01) |
| B29C 39/44 | (2006.01) |
| G05B 19/04 | (2006.01) |
| G01N 1/36 | (2006.01) |
| G01N 35/10 | (2006.01) |
| B29K 91/00 | (2006.01) |
| G01N 35/00 | (2006.01) |

(52) U.S. Cl.
CPC .......... *G05B 19/124* (2013.01); *B29C 39/003* (2013.01); *B29C 39/24* (2013.01); *B29C 39/44* (2013.01); *G01N 1/36* (2013.01); *G01N 35/1009* (2013.01); *G05B 19/0405* (2013.01); *B29K 2091/00* (2013.01); *G01N 2035/00752* (2013.01); *G01N 2035/00772* (2013.01); *G01N 2035/00782* (2013.01); *G05B 2219/23363* (2013.01); *G05B 2219/25294* (2013.01)

(58) Field of Classification Search
None
See application file for complete search history.

(56) References Cited

U.S. PATENT DOCUMENTS

| | | | |
|---|---|---|---|
| 2005/0002828 A1* | 1/2005 | Gunji .................... | B01L 3/0217 422/400 |
| 2005/0029277 A1* | 2/2005 | Tachibana ........... | A61M 5/1456 221/9 |
| 2010/0167334 A1 | 7/2010 | Williamson, IV | |

(Continued)

FOREIGN PATENT DOCUMENTS

| | | |
|---|---|---|
| JP | H0743365 A | 2/1995 |
| JP | 2000305587 A | 11/2000 |
| JP | 2002318177 A | 10/2002 |

*Primary Examiner* — Kristy A Haupt
(74) *Attorney, Agent, or Firm* — Hodgson Russ LLP

(57) ABSTRACT

A control method and a control apparatus for a paraffin dispenser in an embedder, a paraffin dispenser and an embedder are provided. The control method includes: collecting information of a current mold so as to acquire an identification of the current mold; determining whether the identification of the current mold is correct; and controlling the paraffin dispenser to pour paraffin into the current mold, when it is determined that the identification of the current mold is correct.

14 Claims, 4 Drawing Sheets

(56) References Cited

U.S. PATENT DOCUMENTS

| | | |
|---|---|---|
| 2013/0202486 A1 | 8/2013 | Onizawa et al. |
| 2014/0142949 A1* | 5/2014 | Newman .................. G10L 15/26 |
| | | 704/275 |
| 2015/0160104 A1* | 6/2015 | Berberich ................ G01N 1/36 |
| | | 264/279.1 |

* cited by examiner

PARAFFIN DISPENSER, EMBEDDER, AND CONTROL METHOD AND CONTROL APPARATUS FOR PARAFFIN DISPENSER

RELATED APPLICATION

This application claims priority to and benefits of Chinese Patent Application No. 201610145856.7, filed with State Intellectual Property Office on Mar. 15, 2016, the entire content of which is incorporated herein by reference.

TECHNICAL FIELD

The present disclosure relates to a technical field of an embedder for embedding specimens in paraffin, and more particularly to a control method for a paraffin dispenser in an embedder, a control apparatus for a paraffin dispenser in an embedder, a paraffin dispenser and an embedder.

BACKGROUND

An embedder is a device for embedding specimens in paraffin. A paraffin dispenser is widely applied in the embedder to release the melted paraffin into a mold for tissue embedding.

The paraffin dispenser in the related art realizes the paraffin distribution by pushing a paraffin release bracket fixed to the embedder station. This requires the technicians to push the paraffin release bracket while holding the mold with hand, which is lack of humanization and is inconvenient to operate, thus reducing the work efficiency and brining the technicians inconvenience.

SUMMARY

The present disclosure aims to solve at least one of the problems existing in the related art.

Accordingly, a first objective of the present disclosure is to provide a control method for a paraffin dispenser in an embedder, which dispenses the paraffin into the mold intelligently, such that the work efficiency is improved and great convenience is brought to technicians.

A second objective of the present disclosure is to provide a control apparatus for a paraffin dispenser in an embedder.

A third objective of the present disclosure is to provide a paraffin dispenser.

A fourth objective of the present disclosure is to provide an embedder.

In order to achieve the above objectives, according to a first aspect of embodiments of the present disclosure, there is provided a control method for a paraffin dispenser in an embedder. The control method includes: collecting information of a current mold so as to acquire an identification of the current mold; determining whether the identification of the current mold is correct; and controlling the paraffin dispenser to pour paraffin into the current mold, when it is determined that the identification of the current mold is correct.

With the control method for the paraffin dispenser in the embedder according to embodiments of the present disclosure, the identification of the current mold is acquired by collecting the information of the current mold, then it is determined whether the identification of the current mold is correct, and the paraffin dispenser is controlled to pour the paraffin into the current mold when it is determined that the identification of the current mold is correct, such that the paraffin may be dispensed into the mold intelligently and accurately without manual operations from technicians, thus improving the work efficiency greatly and bringing the technicians great convenience.

According to an embodiment of the present disclosure, the information of the current mold is collected by scanning a label of the current mold via a wireless transceiver.

The wireless transceiver scans the label of the current mold by a radio frequency identification technology.

According to another embodiment of the present disclosure, the information of the current mold is collected by scanning a two-dimension code of the current mold via an image acquisition device.

In some embodiments of the present disclosure, the paraffin dispenser is controlled to pour the paraffin into the current mold by opening a flow valve in the paraffin dispenser.

The flow valve is closed, when it is determined that the identification of the current mold is wrong.

According to an embodiment of the present disclosure, it is determined whether the identification of the current mold is correct by determining whether the identification of the current mold matches with a predetermined identification.

In order to achieve the above objectives, according to a second aspect of embodiments of the present disclosure, there is provided a control apparatus for a paraffin dispenser in an embedder. The control apparatus includes: a collecting module, configured to collect information of a current mold so as to acquire an identification of the current mold; and a control module, configured to determine whether the identification of the current mold is correct, and to control the paraffin dispenser to pour paraffin into the current mold when it is determined that the identification of the current mold is correct.

With the control apparatus for the paraffin dispenser in the embedder according to embodiments of the present disclosure, the collecting module acquires the identification of the current mold by collecting the information of the current mold, and then the control module determines whether the identification of the current mold is correct, and controls the paraffin dispenser to pour the paraffin into the current mold when it is determined that the identification of the current mold is correct, such that the paraffin may be dispensed into the mold intelligently and accurately without manual operations from technicians, thus improving the work efficiency greatly and bringing the technicians great convenience. Therefore, the paraffin dispenser, especially the non-touchable paraffin dispenser, has advantages of intelligence, humanization and high-efficiency.

According to an embodiment of the present disclosure, the collecting module includes a wireless transceiver, and the wireless transceiver is configured to scan a label of the current mold, so as to collect the information of the current mold.

The wireless transceiver scans the label of the current mold by a radio frequency identification technology.

According to another embodiment of the present disclosure, the collecting module includes an image acquisition device, and the image acquisition device is configured to scan a two-dimension code of the current mold, so as to collect the information of the current mold.

In some embodiments of the present disclosure, the control module controls the paraffin dispenser to pour the paraffin into the current mold by opening a flow valve in the paraffin dispenser.

The control module controls the flow valve to be closed, when it is determined that the identification of the current mold is wrong.

According to an embodiment of the present disclosure, the control module determines whether the identification of the current mold is correct by determining whether the identification of the current mold matches with a predetermined identification.

In embodiments of the present disclosure, the paraffin dispenser is a non-touchable paraffin dispenser.

Specifically, the non-touchable paraffin dispenser includes a voice recognition paraffin dispenser.

Additionally, embodiments of the present disclosure further provide a paraffin dispenser, including a control apparatus for a paraffin dispenser in an embedder according to above embodiments of the present disclosure.

The paraffin dispenser according to embodiments of the present disclosure may accurately realize an intelligent distribution of the paraffin into the mold by the control apparatus described above, thus greatly improving the work efficiency, bringing the technicians great convenience and providing advantages of intelligence, humanization and high-efficiency.

Finally, embodiments of the present disclosure further provide an embedder, including a paraffin dispenser in an embedder according to above embodiments of the present disclosure.

With the embedder according to embodiments of the present disclosure, the identification of the current mold may be identified intelligently by the paraffin dispenser, especially the non-touchable paraffin dispenser, and the paraffin is poured into the mold only when the identification of the current mold is correct, such that the paraffin may be dispensed into the mold intelligently without manual operations from technicians, thus greatly improving the work efficiency and bringing the technicians great convenience.

DETAILED DESCRIPTION

Reference will now be made in detail to example embodiments, examples of which are illustrated in the accompanying drawings. The following description refers to the accompanying drawings in which the same numbers in different drawings represent the same or similar elements unless otherwise represented. The implementations set forth in the following description of example embodiments do not represent all implementations consistent with the disclosure. Instead, they are merely examples of apparatuses and methods consistent with aspects related to the disclosure as recited in the appended claims.

In the following, a control method for a paraffin dispenser in an embedder, a control apparatus for a paraffin dispenser in an embedder, a paraffin dispenser and an embedder according to embodiments of the present disclosure will be described in detail with reference to drawings.

Figure 1:
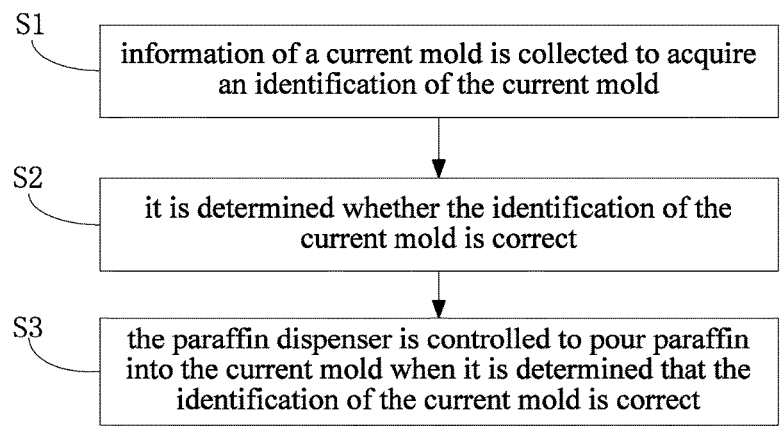
FIG. 1 is a flow chart of a control method for a paraffin dispenser in an embedder according to an embodiment of the present disclosure.

FIG. 1 is a flow chart of a control method for a paraffin dispenser in an embedder according to an embodiment of the present disclosure. As shown in FIG. 1, the control method includes following steps.

In step S1, information of a current mold is collected to acquire an identification of the current mold.

The paraffin dispenser may be a non-touchable paraffin dispenser, and the non-touchable paraffin dispenser may include a voice recognition paraffin dispenser.

According to an embodiment of the present disclosure, the information of the current mold may be collected by scanning a label of the current mold via a wireless transceiver.

Specifically, the wireless transceiver may scan the label of the current mold by a radio frequency identification (RFID) technology. That is, the wireless transceiver may be a reader, the label of the current mold may be a responder, and the reader communicates with the responder wirelessly, for example, has an information interchange with the responder via a half-duplex communication mode. From a view of an energy induction mode and a communication mode between a RFID card reader and an electronic label, two kinds of couplings are provided, i.e. an inductive coupling and a back scattering coupling. The RFID with low frequency typically uses the former one, while the RFID with high frequency typically uses the latter one. The reader typically includes a coupling unit, a transceiver, a control unit and an interface unit. The responder is an information carrier under the RFID technology. The present responder typically is a passive unit including a coupling element (such as an induction coil) and a microchip.

It should be understood that, the wireless transceiver may be provided with an infrared sensor and may collect the information of the current mold by an infrared scanning technology.

According to another embodiment of the present disclosure, the information of the current mold may be collected by scanning a two-dimension code of the current mold with an image acquisition device, such as a camera, i.e. the identification of the current mold is identified by a two-dimension code identification technology.

In step S2, it is determined whether the identification of the current mold is correct.

Further, it may be determined whether the identification of the current mold is correct by determining whether the identification of the current mold matches with a predetermined identification.

In other words, identifications of various molds may be pre-stored in a control module, such as a controller. In this way, it may be determined whether the identification of the current mold is correct by determining whether the identification of the current mold matches with the predetermined identification (i.e., the identification pre-stored in the control module).

In step S3, the paraffin dispenser is controlled to pour paraffin into the current mold when it is determined that the identification of the current mold is correct.

According to an embodiment of the present disclosure, the paraffin dispenser may be controlled to pour paraffin into the current mold by opening a flow valve in the paraffin dispenser.

When it is determined that the identification of the current mold is wrong, the flow valve is closed, such that the paraffin dispenser cannot pour paraffin into the current mold.

Figure 2:
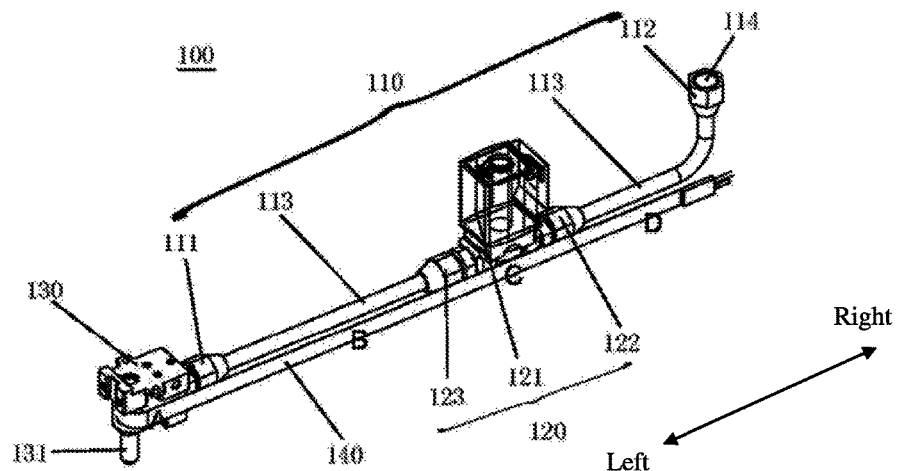
FIG. 2 is a schematic view showing a paraffin dispenser in an embedder according to an embodiment of the present disclosure.
Figure 3:
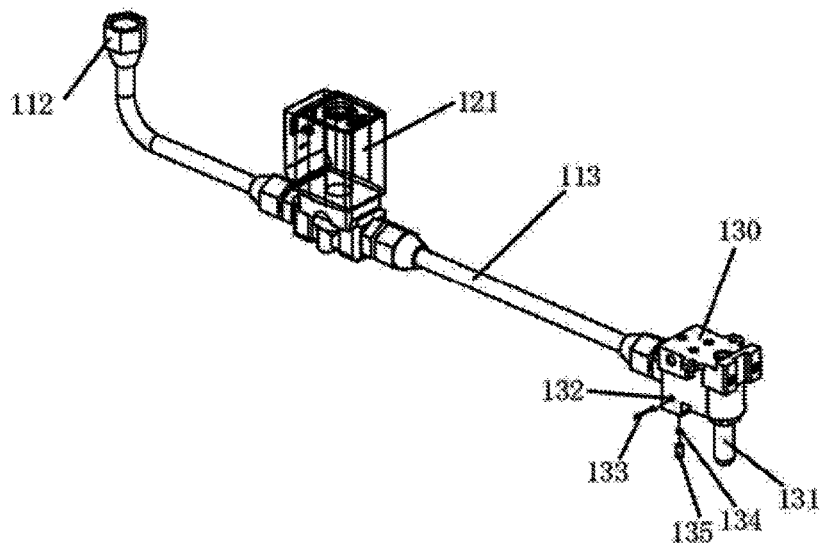
FIG. 3 is a schematic view showing a paraffin dispenser in an embedder according to an embodiment of the present disclosure, from another perspective, in which a heating strip is not shown.

Specifically, as shown in FIGS. 2 and 3, a paraffin dispenser 100 in an embedder according to some specific embodiments of the present disclosure includes a distribution tube 110, a flow valve 120, a paraffin outlet member 130 and a heating strip 140. The distribution tube 110 includes a first end 111 (a left end in FIG. 2), a second end 112 (a right end in FIG. 2) and a tube body 113. In the embodiments shown in FIG. 2 and FIG. 3, the tube body 113 is a circular tube, i.e. the tube body 113 has a circular cross section, but the present disclosure is not limited to this. For example, the tube body 113 may have a cross section of another shape, like a rectangular cross section.

The flow valve 120 is disposed on the distribution tube 110. Specifically, the flow valve 120 is disposed in the substantial middle of the distribution tube 110 and close to the right end of the distribution tube 110, as shown in FIG. 2. It should be understood by those skilled in the art that the present disclosure does not particularly limit an installation position of the flow valve 120.

The flow valve 120 includes a valve body 121, an inlet tube 122 and an outlet tube 123. The valve body 121 includes an outlet and an inlet (not shown), and the inlet tube 122 has a first end (a left end of the inlet tube 122 in FIG. 2) connected with the inlet of the valve body 121 and a second end (a right end of the inlet tube 122 in FIG. 2) connected with the tube body 113 of the distribution tube 110.

The outlet tube 123 has a first end (a right end of the outlet tube 123 in FIG. 2) connected with the outlet of the valve body 121 and a second end (a left end of the outlet tube 123 in FIG. 2) connected with the tube body 113 of the distribution tube 110. In this embodiment, an axis of the outlet tube 123 is collinear with that of the inlet tube 122. However, it can be understood by those skilled in the art that the axis of the outlet tube 123 may be not collinear with that of the inlet tube 122.

As shown in FIG. 2, the heating strip 140 is stuck to the tube body 113 and the first end 111 of the distribution tube 110, the inlet tube 122 and the outlet tube 123 of the flow valve 120, and the paraffin outlet member 130. It can be understood by those skilled in the art that a left end of the heating strip 140 may enclose at least a part of a peripheral surface of the paraffin outlet member 130. For example, the left end of the heating strip 140 is configured to have a U shape.

In some preferred embodiments of the present disclosure, as shown in FIG. 2, the heating strip 140 has different heating powers in four positions (A, B, C and D) on the distribution tube 110, the flow valve 120 and the paraffin outlet member 130, so as to keep a uniform temperature in each position. The heating powers of the heating strip 140 in different positions may be calculated according to materials and volumes of the distribution tube 110, the flow valve 120 and the paraffin outlet member 130. Preferably, since the flow valve 120 and the paraffin outlet member 130 both have a relatively large volume, and the paraffin is distributed from the paraffin outlet member 130, a first portion of the heating strip 140 stuck to the paraffin outlet member 130 (i.e. located at position A) has a first heating power greater than other portions of the heating strip 140, so as to prevent the paraffin from being solidified and overheated during distribution thereof. A second portion of the heating strip 140 stuck to the flow valve 120 (i.e. located at position C) has a second heating power greater than a third portion of the heating strip 140 stuck to the distribution tube 110 (i.e. located at positions B and D), but less than the first portion of the heating strip 140 stuck to the paraffin outlet member 130. In this way, the paraffin can flow smoothly and a flow rate of the paraffin can be measured accurately, so as to improve a distribution effect, avoid blockage due to solidification of the paraffin and prevent the paraffin from being overheated.

Accordingly, the paraffin dispenser may be controlled to pour or not pour the paraffin into the current mold by controlling the flow valve 120 to be opened or closed.

Figure 4:
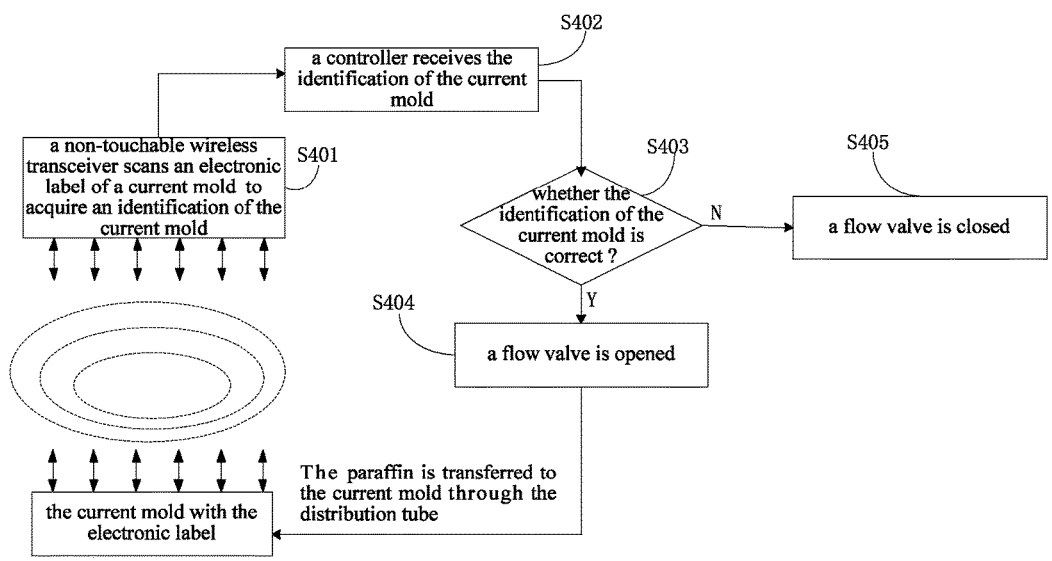
FIG. 4 is a flow chart of a control method for a paraffin dispenser in an embedder according to a specific embodiment of the present disclosure.

Specifically, according to an embodiment of the present disclosure, as shown in FIG. 4, the above-described control method for the paraffin dispenser in the embedder may include following steps.

In step S401, a non-touchable wireless transceiver disposed on the paraffin dispenser scans an electronic label of a current mold via a RFID technology, so as to acquire an identification of the current mold. The electronic label of the current mold is configured to contain the identification of the current mold, such as an electronic code.

In step S402, a controller receives the identification of the current mold.

In step S403, the controller determines whether the identification of the current mold is correct, i.e. whether the identification of the current mold matches with a pre-stored identification of a corresponding mold, in which the corresponding mold is intended to be provided with paraffin. If yes, step S404 is executed, or else, step S405 is executed.

In step S404, the paraffin dispenser is switched on, for example a flow valve disposed on a distribution tube of the paraffin dispenser is opened, such that the paraffin is transferred to the current mold through the distribution tube.

In step S405, the flow valve is closed.

In conclusion, in the control method for the paraffin dispenser according to embodiments of the present disclosure, it is firstly determined whether the identification of the current mold is correct via the wireless scanning technology, if yes, the flow valve is opened to dispense the paraffin into the corresponding mold intelligently, such that manual operations from technicians are not required, and thus the paraffin dispenser, especially the non-touchable paraffin dispenser, has advantages of intelligence, humanization and high-efficiency.

With the control method for the paraffin dispenser in the embedder according to embodiments of the present disclosure, the identification of the current mold is acquired by collecting the information of the current mold, then it is determined whether the identification of the current mold is correct, and the paraffin dispenser is controlled to pour the paraffin into the current mold when it is determined that the identification of the current mold is correct, such that the paraffin may be dispensed into the mold intelligently and accurately without manual operations from technicians, thus greatly improving the work efficiency and bringing great convenience to the technicians.

Figure 5:
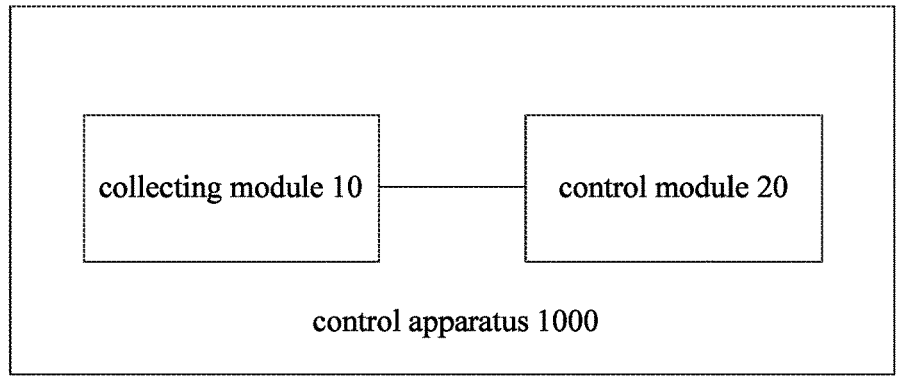
FIG. 5 is a block diagram of a control apparatus for a paraffin dispenser in an embedder according to an embodiment of the present disclosure.

FIG. 5 is a block diagram of a control apparatus 1000 for a paraffin dispenser in an embedder according to an embodiment of the present disclosure. As shown in FIG. 5, the control apparatus 1000 includes a collecting module 10 and a control module 20, such as a controller.

The collecting module 10 is configured to collecting information of a current mold so as to acquire an identification of the current mold. The control module 20 is configured to determine whether the identification of the current mold is correct, and to control the paraffin dispenser to pour paraffin into the current mold when it is determined that the identification of the current mold is correct.

Figure 6:
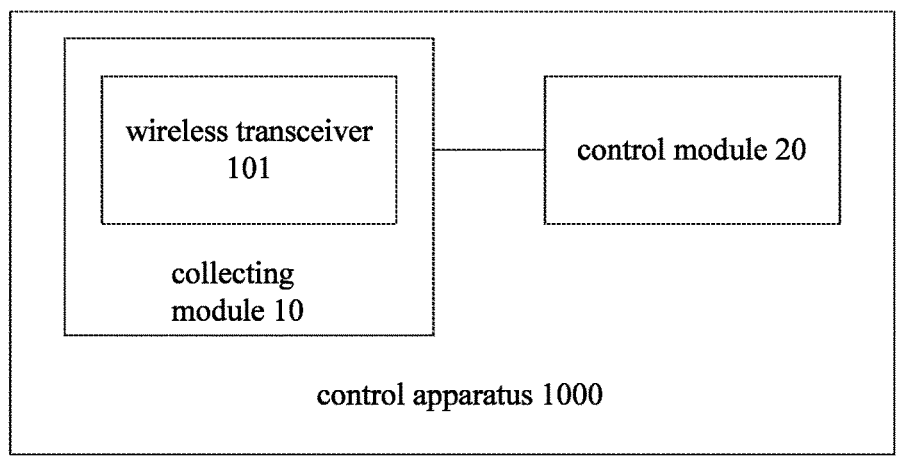
FIG. 6 is a block diagram of a control apparatus for a paraffin dispenser in an embedder according to a specific embodiment of the present disclosure.

Further, according to a specific embodiment of the present disclosure, as shown in FIG. 6, the collecting module 10 includes a wireless transceiver 101. The wireless transceiver 101 is configured to scan a label of the current mold, such that the collecting module 10 collects the information of the current mold via the wireless transceiver 101, and thus acquires the identification of the current mold according to the information collected.

The wireless transceiver 101 may scan the label of the current mold via a RFID technology, such that the collecting module 10 acquires the identification of the current mold according to the scanned label information.

Figure 7:
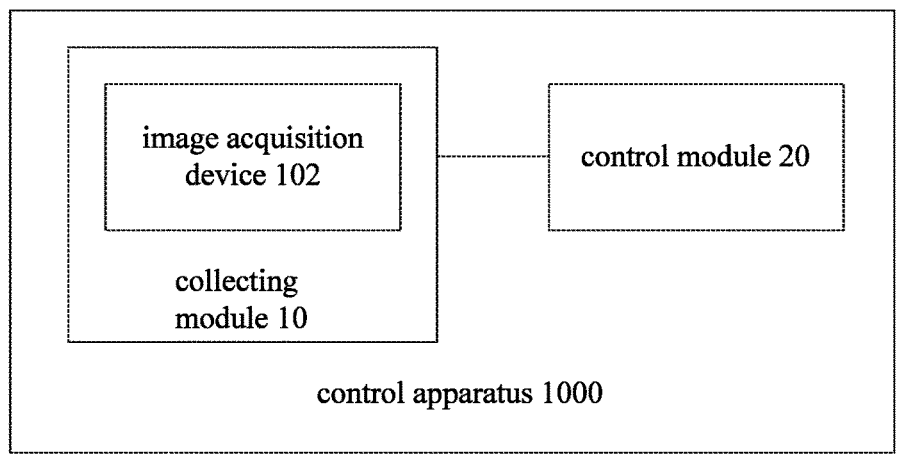
FIG. 7 is a block diagram of a control apparatus for a paraffin dispenser in an embedder according to another specific embodiment of the present disclosure.

According to another specific embodiment of the present disclosure, as shown in FIG. 7, the collecting module 10 includes an image acquisition device 102, such as a camera. The image acquisition device 102 is configured to scan a two-dimension code of the current mold, such that the collecting module 10 collects the information of the current mold via the image acquisition device 102, and thus acquires the identification of the current mold according to the information collected.

According to some specific embodiments of the present disclosure, as shown in FIG. 2 and FIG. 3, the paraffin dispenser in the embedder includes a distribution tube 110 and a flow valve 120 disposed on the distribution tube 110. The flow valve 120 is under the control of the control module 20, such that the control module 20 controls the paraffin dispenser to pour paraffin into the current mold by opening the flow valve 120 in the paraffin dispenser.

When it is determined that the identification of the current mold is wrong, the control module 20 controls the flow valve 120 to be closed.

Specifically, identifications of various molds may be pre-stored in the control module 20, such as a controller, such that the control module 20 may determine whether the identification of the current mold is correct by determining whether the identification of the current mold matches with a predetermined identification (i.e., the identification pre-stored in the control module), and further control different amounts of paraffin to be poured into different molds, thus realizing an intelligent control on the paraffin dispenser.

In embodiments of the present disclosure, the paraffin dispenser may be a non-touchable paraffin dispenser. For example, the non-touchable paraffin dispenser may include a voice recognition paraffin dispenser.

With the control apparatus for the paraffin dispenser in the embedder according to embodiments of the present disclosure, the collecting module acquires the identification of the current mold by collecting the information of the current mold, and the control module determines whether the identification of the current mold is correct and controls the paraffin dispenser to pour paraffin into the current mold when it is determined that the identification of the current mold is correct, such that the paraffin may be dispensed into the mold intelligently without manual operations from technicians, thus greatly improving the work efficiency and bringing the technicians great convenience. Therefore, the paraffin dispenser, especially the non-touchable paraffin dispenser, has advantages of intelligence, humanization and high-efficiency.

Figure 8:
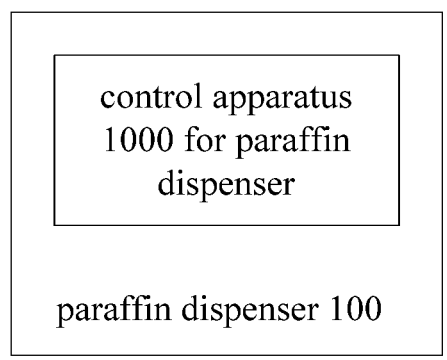
FIG. 8 is a block diagram of a paraffin dispenser according to an embodiment of the present disclosure.

Additionally, as shown in FIG. 8, embodiments of the present disclosure further provide a paraffin dispenser 100, including a control apparatus 1000 for a paraffin dispenser in an embedder according to above embodiments of the present disclosure.

The paraffin dispenser according to embodiments of the present disclosure may dispense the paraffin into the mold intelligently and accurately through the control apparatus described above, so as to improve the work efficiency greatly, bring the technicians great convenience and provide advantages of intelligence, humanization and high-efficiency.

Figure 9:
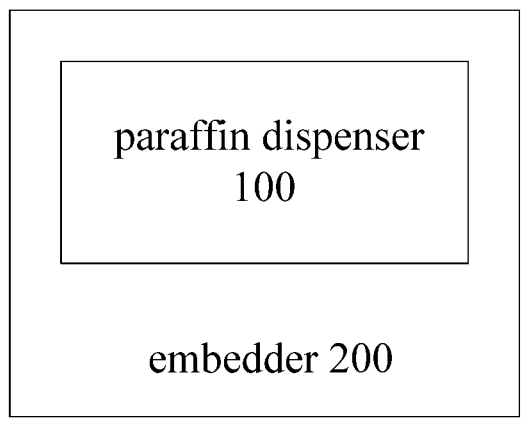
FIG. 9 is a block diagram of an embedder according to an embodiment of the present disclosure.

Finally, as shown in FIG. 9, embodiments of the present disclosure further provide an embedder 200, including a paraffin dispenser 100 according to above embodiments of the present disclosure.

With the embedder 200 according to embodiments of the present disclosure, the identification of the current mold may be identified intelligently by the paraffin dispenser, especially the non-touchable paraffin dispenser, and the paraffin is poured into the mold only when the identification of the current mold is correct, such that the paraffin may be dispensed into the mold intelligently and accurately without manual operations from technicians, thus greatly improving the work efficiency and bringing the technicians great convenience.

In the specification, it is to be understood that terms such as "central," "longitudinal," "lateral," "length," "width," "thickness," "upper," "lower," "front," "rear," "left," "right," "vertical," "horizontal," "top," "bottom," "inner," "outer," "clockwise," and "counterclockwise" should be construed to refer to the orientation as then described or as shown in the drawings under discussion. These relative terms are for convenience of description and do not require that the present disclosure be constructed or operated in a particular orientation.

In addition, terms such as "first" and "second" are used herein for purposes of description and are not intended to indicate or imply relative importance or significance. Thus, the feature defined with "first" and "second" may comprise one or more this feature. In the description of the present disclosure, "a plurality of" means two or more than two, unless specified otherwise.

In the present disclosure, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

In the present disclosure, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A control method for a paraffin dispenser in an embedder, comprising:
    collecting information of a current mold while the current mold is in the paraffin dispenser so as to acquire an identification of the current mold;
    determining whether the identification of the current mold is correct by determining whether the identification of the current mold matches with a predetermined identification; and
    controlling the paraffin dispenser to pour paraffin into the current mold, when it is determined that the identification of the current mold is correct,
    wherein the paraffin dispenser is controlled to pour the paraffin into the current mold by opening a flow valve in the paraffin dispenser,
    wherein the flow valve is not opened when it is determined that the identification of the current mold is not correct.

2. The control method according to claim 1, wherein the information of the current mold is collected by scanning a label of the current mold via a wireless transceiver.

3. The control method according to claim 2, wherein the wireless transceiver scans the label of the current mold by a radio frequency identification technology.

4. The control method according to claim 1, wherein the information of the current mold is collected by scanning a two-dimension code of the current mold via an image acquisition device.

5. A control apparatus for a paraffin dispenser in an embedder, comprising:
    a collecting module, configured to collect information of a current mold while the current mold is in the paraffin dispenser so as to acquire an identification of the current mold; and
    a control module, configured to determine whether the identification of the current mold is correct by determining whether the identification of the current mold matches with a predetermined identification, and to control the paraffin dispenser to pour paraffin into the current mold when it is determined that the identification of the current mold is correct,
    wherein the control module controls the paraffin dispenser to pour the paraffin into the current mold by opening a flow valve in the paraffin dispenser,
    wherein the control module does not open the flow valve when it is determined that the identification of the current mold is not correct.

6. The control apparatus according to claim 5, wherein the collecting module comprises a wireless transceiver, and the wireless transceiver is configured to scan a label of the current mold, so as to collect the information of the current mold.

7. The control apparatus according to claim 6, wherein the wireless transceiver scans the label of the current mold by a radio frequency identification technology.

8. The control apparatus according to claim 5, wherein the collecting module comprises an image acquisition device, and the image acquisition device is configured to scan a two-dimension code of the current mold, so as to collect the information of the current mold.

9. The control apparatus according to claim 5, wherein the control module determines whether the identification of the current mold is correct by determining whether the identification of the current mold matches with a predetermined identification.

10. The control apparatus according to claim 5, wherein the paraffin dispenser is a non-touchable paraffin dispenser.

11. The control apparatus according to claim 10, wherein the non-touchable paraffin dispenser comprises a voice recognition paraffin dispenser.

12. A paraffin dispenser, comprising a control apparatus for a paraffin dispenser in an embedder, wherein the control apparatus comprises:
    a collecting module, configured to collect information of a current mold while the current mold is in the paraffin dispenser so as to acquire an identification of the current mold; and
    a control module, configured to determine whether the identification of the current mold is correct by determining whether the identification of the current mold matches with a predetermined identification, and to control the paraffin dispenser to pour paraffin into the current mold when it is determined that the identification of the current mold is correct,
    wherein the control module controls the paraffin dispenser to pour the paraffin into the current mold by opening a flow valve in the paraffin dispenser,
    wherein the control module does not open the flow valve when it is determined that the identification of the current mold is not correct.

13. The paraffin dispenser according to claim 12, wherein the collecting module comprises a wireless transceiver, and the wireless transceiver is configured to scan a label of the current mold, so as to collect the information of the current mold.

14. The paraffin dispenser according to claim 12, wherein the collecting module comprises an image acquisition device, and the image acquisition device is configured to scan a two-dimension code of the current mold, so as to collect the information of the current mold.

* * * * *